US00PP14748P2

(12) United States Plant Patent
Miyano

(10) Patent No.: US PP14,748 P2
(45) Date of Patent: May 4, 2004

(54) PETUNIA PLANT NAMED KEIPABUKAS

(50) Latin Name: *Petunia×hybrida*
Varietal Denomination: Keipabukas

(75) Inventor: Shinya Miyano, Tonosho-machi (JP)

(73) Assignee: Keisei Rose Nurseries, Inc., Tokyo (JP)

( * ) Notice: Subject to any disclaimer, the term of this patent is extended or adjusted under 35 U.S.C. 154(b) by 0 days.

(21) Appl. No.: 10/243,317

(22) Filed: Sep. 12, 2002

(51) Int. Cl.[7] ..... A01H 5/00
(52) U.S. Cl. ..... Plt./356

(58) Field of Search ..... Plt./356

(56) References Cited

PUBLICATIONS http://www.nickys–nursery.co.uk/seeds/pages/2003.htm.*
UPOV ROM GTITM Computer Database, GTI JOUVE Retrieval Software, citation(s) for 'Keipabukas'.*

* cited by examiner

*Primary Examiner*—Bruce R. Campell
*Assistant Examiner*—W C Haas
(74) *Attorney, Agent, or Firm*—Klarquist Sparkman LLP

(57) ABSTRACT

Petunia plant having a free flowering, pendant habit and free branching growth habit.

2 Drawing Sheets

Genus and species: Petunia×hybrida.
Variety denomination: 'Keipabukas'.

SUMMARY OF THE INVENTION

The present invention relates to a new and distinct variety of petunia plant which was originated by me by crossing two unnamed varieties, neither of which is patented.

BACKGROUND OF THE INVENTION

The primary objective of this breeding was to produce a new petunia variety having a free flowering, pendant habit and free branching.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Vigorous habit; and
2. Profuse flowering.

Asexual reproduction of this new variety by cuttings, as performed at Yachigo-shi, Chiba-ken, Japan shows that the foregoing and all other characteristics and distinctions come true to form and are established and transmitted through succeeding propagations.

DETAILED BOTANICAL DESCRIPTION

The following is a detailed description of my new petunia cultivar with color descriptions using terminology in accordance with The Royal Horticultural Society (London) Colour Chart (2001), except where ordinary dictionary significance of color is indicated.

In the attached photographs

Figure 1:
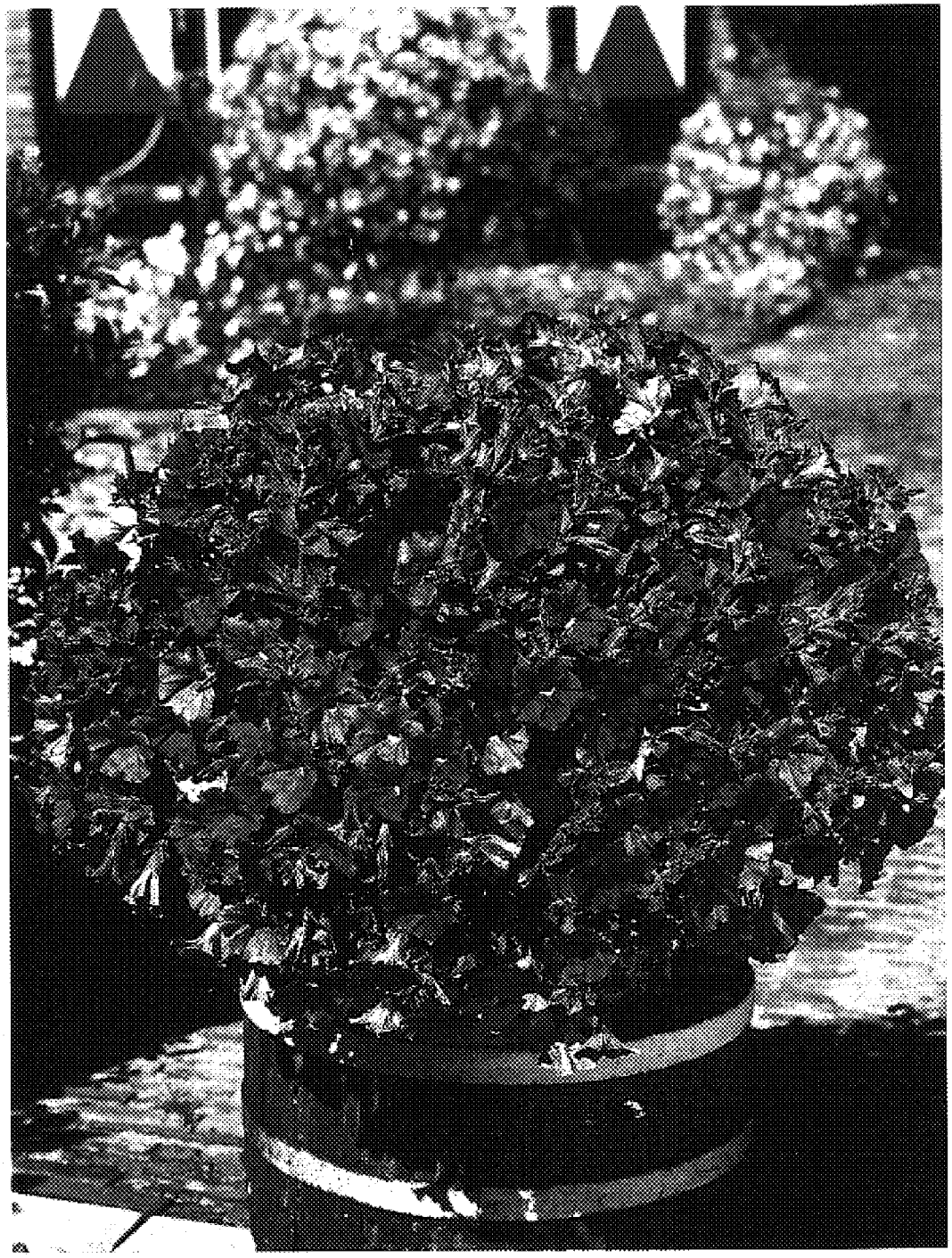
Figure 2:
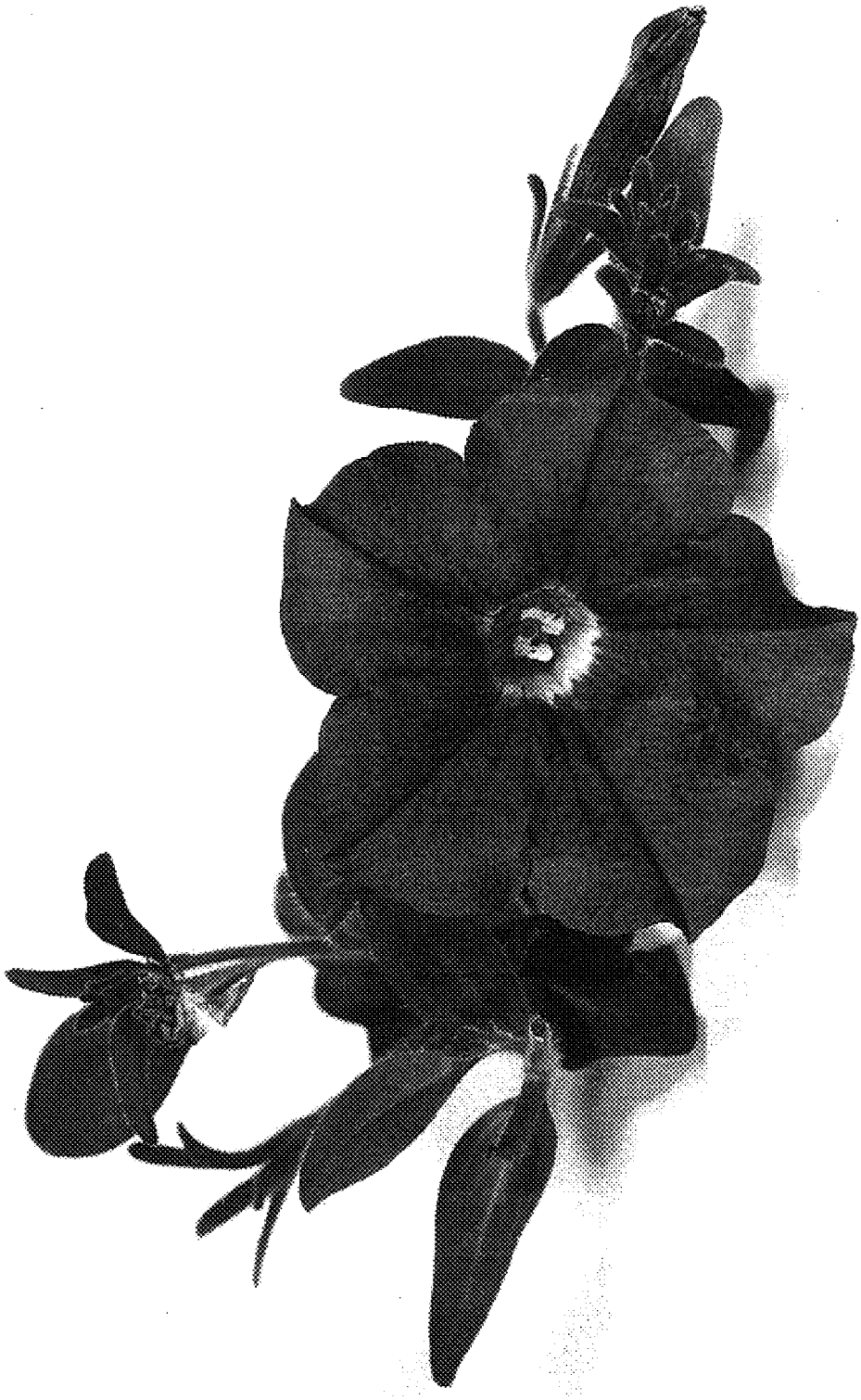

FIG. 1 is a view of the entire plant grown in a planter in a garden environment, and FIG. 2 is an enlarged view of a portion of the plant showing a flower and a portion of the foliage.

Parentage:
*Seed parent.*—Unnamed seedling.
*Pollen parent.*—Unnamed seedling.
Classification:
*Botanical.*—Petunia×hybrida.
*Commercial.*—Petunia.

FLOWER

Observations made from plants sixteen weeks of age grown in a garden environment in Chibo-Kan, Japan and Somis, Calif.

Blooming habit: Continuous, late June to October in Chibo-Kan, Japan and as long as climate permits in the United States.

Plant:
*Growth habit.*—Vigorous.
*Mature plant.*—Height: 30 cm. at 14–16 weeks of age. Spread: 50–60 cm in diameter.

Stems: Overall Length: 25 to 25 cm. Thickness: 2.5 to 3.0 mm. Color: Yellow-Green Group 146C. Pubescence: Pubescent. Mode of Branching: Abundant. Length of Internode: 2.5 to 4.0 cm.

Leaf: Phyllotaxis: Alternate. Overall Shape: Elliptic. Base Shape: Cuneate. Apex Shape: Acute. Margin shape: Smooth with a few fine hairs on the margin. Size: Width: 2.8 cm; Length: 5.5 cm. Thickness: 0.4–0.5 mm. Color: Upper surface: Yellow-Green Group 146A to 146B. Lower surface: Yellow-Green Group 146B. Pubescence: Puberulent and slightly glutinous. Venation Pattern: Reticulate. Vein color: Yellow-Green Group 146C.
*Petiole.*—Length: 3–4 mm. Diameter: 2 mm. Color: Yellow-Green Group 146C.

Flower:
*Bud length.*—1 cm.
*Bud diameter.*—5 mm.
*Bud shape.*—Cigar shaped.

*Bud color.*—Violet Group 86A.

*Texture.*—Velutinous.

*Size.*—Average open diameter length: 38–40 mm.

*Type.*—Single.

*Shape.*—Flower is a fused petal in funnel form shape.

*Peduncle.*—Length: 1.7 cm. Diameter: 2.2 mm. Color: Yellow-Green Group 145A to 145B. Texture: Pubescent. Smooth.

*Calyx.*—No. of sepals: 5. Sepal length: 17–19 mm. Sepal shape: Linear with rounded apex. Inner color: Yellow Green 147B. Outer color: Yellow Green 147C.

*Corolla.*—Length: 4.6–4.8 cm. Diameter: 3.6–3.8 cm. Color: Violet Group N88C at outer end fading to Violet Group N88B toward base; base is White Group 155A.

*Flowering type.*—Dehiscent. Flowers at 16 weeks, 120–140 flowers per plant. Flowers do not require pinching.

Petal:

*Color.*—Upper Surface: Violet Group N88A at outer end fading to Violet Group N88B toward base with throat of White Group N155. Lower Surface: Violet Group N88C at outer end changing to Violet Blue Group 91B toward base with prominent veins of Violet Blue Group 91A.

Reproductive parts:

*Stamens.*—Quantity: Five. Anther: Color: Greyed-Yellow Group 161D. Filament: Color: Violet Group 86A at upper end fading to Violet Group 85D at base.

*Pistil.*—Quantity: One. Stigma color: Greyed-Yellow Group 160C. Style color: Yellow-Green Group 144D.

*Fruit.*—None observed.

Disease resistance: Resistant to powdery mildew under normal growing conditions.

Fragrance: Light spicy scent.

I claim:

1. A new and distinct variety of petunia plant, substantially as herein shown and described, characterized particularly by its free flowering, pendant habit and free branching growth habit.

* * * * *